US011610671B2

(12) United States Patent
Hochworter

(10) Patent No.: US 11,610,671 B2
(45) Date of Patent: Mar. 21, 2023

(54) SYSTEM AND METHOD FOR LOCATING EQUIPMENT IN A HEALTHCARE FACILITY

(71) Applicant: Hill-Rom Services, Inc., Batesville, IN (US)

(72) Inventor: Ryan Hochworter, Alpharetta, GA (US)

(73) Assignee: Hill-Rom Services, Inc., Batesville, IN (US)

( * ) Notice: Subject to any disclaimer, the term of this patent is extended or adjusted under 35 U.S.C. 154(b) by 407 days.

(21) Appl. No.: 17/015,209

(22) Filed: Sep. 9, 2020

(65) Prior Publication Data

US 2021/0098119 A1 Apr. 1, 2021

Related U.S. Application Data

(60) Provisional application No. 62/906,331, filed on Sep. 26, 2019.

(51) Int. Cl.
| | | |
|---|---|---|
| *G16H 40/20* | (2018.01) | |
| *G16H 40/40* | (2018.01) | |
| *G06K 7/14* | (2006.01) | |
| *G06Q 50/28* | (2012.01) | |
| *G06Q 30/018* | (2023.01) | |

(52) U.S. Cl.
CPC ........... *G16H 40/20* (2018.01); *G06K 7/1413* (2013.01); *G06Q 30/0185* (2013.01); *G06Q 50/28* (2013.01); *G16H 40/40* (2018.01)

(58) Field of Classification Search
CPC ........ G16H 40/20; G16H 40/40; G16H 40/67; G06K 7/1413; G06Q 30/0185; G06Q 50/28
See application file for complete search history.

(56) References Cited

U.S. PATENT DOCUMENTS

| | | | |
|---|---|---|---|
| 3,439,320 A | 4/1969 | Ward | |
| 4,225,953 A | 9/1980 | Simon et al. | |
| 5,062,151 A | 10/1991 | Shipley | |
| 5,218,344 A | 6/1993 | Ricketts | |
| 5,291,399 A | 3/1994 | Chaco | |
| 5,699,038 A | 12/1997 | Ulrich et al. | |

(Continued)

FOREIGN PATENT DOCUMENTS

| | | |
|---|---|---|
| EP | 1889222 A2 | 2/2008 |
| EP | 2273402 A1 | 1/2011 |

(Continued)

OTHER PUBLICATIONS

Ross, Ian. "Containing infection through GIS; pilot program planned for Sault hospital." Northern Ontario Business: 29.2: 15(2). Laurentian Business Publishing, Inc. (Dec. 2008) (Year: 2008).*

*Primary Examiner* — Linh Giang Le
(74) *Attorney, Agent, or Firm* — Barnes & Thornburg LLP

(57) ABSTRACT

An equipment locating system includes a plurality of medical apparatuses required for patient treatment and having equipment tags. A real-time locating system is configured to determine a location of each of the plurality of medical apparatuses by receiving a signal from the equipment tags. The caregiver selects a medical apparatus from an apparatus list when the medical apparatus is acquired so that the medical apparatus is tagged as being checked out.

20 Claims, 9 Drawing Sheets

(56) References Cited

U.S. PATENT DOCUMENTS

| | | | |
|---|---|---|---|
| 6,252,512 | B1 | 6/2001 | Riley |
| 6,344,794 | B1 | 2/2002 | Ulrich et al. |
| 6,747,556 | B2 | 6/2004 | Mederna et al. |
| 6,937,150 | B2 | 8/2005 | Medema et al. |
| 6,972,683 | B2 | 12/2005 | Lestienne et al. |
| 9,830,424 | B2 | 11/2017 | Dixon et al. |
| 10,376,169 | B2 | 8/2019 | Kaib et al. |
| 2003/0025602 | A1 | 2/2003 | Medema et al. |
| 2004/0019258 | A1 | 1/2004 | Kavounas et al. |
| 2004/0049233 | A1 | 3/2004 | Edwards |
| 2005/0035862 | A1 * | 2/2005 | Wildman ........... G08B 13/2462 340/572.1 |
| 2006/0181243 | A1 | 8/2006 | Graves et al. |
| 2006/0181424 | A1 | 8/2006 | Graves et al. |
| 2006/0183426 | A1 | 8/2006 | Graves et al. |
| 2006/0185005 | A1 | 8/2006 | Graves et al. |
| 2006/0236373 | A1 | 10/2006 | Graves et al. |
| 2007/0004389 | A1 | 1/2007 | Wallace et al. |
| 2008/0126126 | A1 | 5/2008 | Ballai |
| 2013/0124227 | A1 | 5/2013 | Ellis |

FOREIGN PATENT DOCUMENTS

| | | | |
|---|---|---|---|
| EP | 2733631 A1 | 5/2014 | |
| WO | WO-2008063936 A2 * | 5/2008 | ........... G06F 19/327 |
| WO | 2011037883 A2 | 3/2011 | |

* cited by examiner

SYSTEM AND METHOD FOR LOCATING EQUIPMENT IN A HEALTHCARE FACILITY

CROSS-REFERENCE TO RELATED APPLICATIONS

This application claims priority under 35 U.S.C. § 119(e) to U.S. Provisional Patent Application Ser. No. 62/906,331, filed Sep. 26, 2019, which is expressly incorporated by reference herein.

TECHNICAL FIELD

The present disclosure relates to devices, systems, and methods for a real-time locating system in a healthcare facility. More specifically, the present disclosure relates to devices, systems, and methods for locating equipment with a real-time locating system in a healthcare facility.

BACKGROUND

During rounds at a healthcare facility, caregivers are required to perform multiple tasks for multiple patients. Organizing the tasks can be challenging for caregivers. Complicating these challenges, the equipment required for each task may be at any location within the healthcare facility. Caregivers spend significant time and resources locating equipment required for patient care. Often, the required equipment is in use or otherwise unavailable. Caregivers require a system to optimize the ability to locate equipment related to tasks at the healthcare facility.

SUMMARY

The present disclosure includes one or more of the features recited in the appended claims and/or the following features which, alone or in any combination, may comprise patentable subject matter.

According to a first aspect of the disclosed embodiments, an equipment locating system may include a plurality of medical apparatuses required for patient treatment and having equipment tags. A real-time locating system may be configured to determine a location of each of the plurality of medical apparatuses by receiving a signal from the equipment tags. A display may be configured to display a caregiver menu to select a type of caregiver. The display may display a patient menu listing patients under the care of the type of caregiver selected from the caregiver menu. The display may display a task menu listing tasks associated with a patient selected from the patient menu. A medical apparatus of the plurality of medical apparatuses may be required for the task. The display may display an apparatus list listing the medical apparatus required for the task along with a corresponding location of the medical apparatus as provided by the real-time locating system. The caregiver may select the medical apparatus from the apparatus list when the medical apparatus is acquired so that the medical apparatus is tagged as being checked out.

In this aspect, the real-time locating system may include a high-accuracy locating system such as an ultra-wideband (UWB) locating system, radio detection and ranging (RADAR) equipment or cameras and/or other imaging equipment or other high-accuracy locating technologies. The medical apparatuses may include, but are not limited to, a mobile lift, a walker, a patient bed, a scanner, for example, a bladder scanner, a glucometer, a respiratory therapy, a VSM, a PCA pump, an spO2 monitor, a language translator, or a fall camera. The display may include a touchscreen display or a display having user inputs, for example, buttons.

In some embodiments of this aspect, the medical apparatus may include a bar code and the caregiver may scan the bar code to tag the medical apparatus as being checked out. The type of caregiver may include at least one of a doctor, a nurse, a technician, or a housekeeper. The medical apparatus of the plurality of medical apparatuses may include more than one medical apparatus. Each of the more than one medical apparatus may be displayed in the apparatus list. The display may list the location of the medical apparatus that is closest to the caregiver. The location of the caregiver may be determined by the real-time locating system.

Optionally, in this aspect, a caregiver tag may be provided. The real-time locating system may determine the location of the caregiver based on a signal received from the caregiver tag. The caregiver tag may be at least one of a lanyard or a bracelet. The display may list the location of the medical apparatus that is closest to the patient's room. Each medical apparatus of the plurality of medical apparatuses may be tagged as at least one of checked in, checked out, or requires cleaning. The apparatus list may include medical apparatuses that are tagged as checked in. The caregiver may tag the medical apparatus as checked in when the caregiver is finished using the medical apparatus. The caregiver may tag the medical apparatus as requires cleaning when the caregiver is finished using the medical apparatus.

It may be desired, in this aspect, that the apparatus list includes a first medical apparatus and a second medical apparatus that is located near the first medical apparatus. The display may list a first medical apparatus and a second medical apparatus that are located in the same room. The display may list a first medical apparatus and a second medical apparatus that are located in the same area of a healthcare facility.

According to a second aspect of the disclosed embodiments, an equipment locating system may include a caregiver tag coupled to a caregiver in a healthcare facility. A real-time locating system may be configured to determine a location of the caregiver based on a signal received from the caregiver tag. A display may be configured to notify the caregiver of a task for a patient when the caregiver is determined by the real-time locating system to be within a predetermined proximity of a patient's room. The display may display an apparatus list listing a medical apparatus required for the task along with a corresponding location of the medical apparatus as provided by the real-time locating system. The caregiver may select the medical apparatus from the apparatus list when the medical apparatus is acquired so that the medical apparatus is tagged as being checked out.

In this aspect, the real-time locating system may include a high-accuracy locating system such as an ultra-wideband (UWB) locating system, radio detection and ranging (RADAR) equipment or cameras and/or other imaging equipment or other high-accuracy locating technologies. The medical apparatuses may include, but are not limited to, a mobile lift, a walker, a patient bed, a scanner, for example, a bladder scanner, a glucometer, a respiratory therapy, a VSM, a PCA pump, an spO2 monitor, a language translator, or a fall camera. The display may include a touchscreen display or a display having user inputs, for example, buttons.

In some embodiments of this aspect, the caregiver tag may be at least one of a lanyard or a bracelet. The apparatus list may include a medical apparatus that is closest to the caregiver. The apparatus list may include a medical apparatus that is closest to the patient's room. The apparatus list may include a medical apparatus that is tagged as being checked in. The caregiver may tag the medical apparatus as being checked in when the caregiver is finished using the medical apparatus. The caregiver may tag the medical apparatus as requires cleaning when the caregiver is finished using the medical apparatus.

Optionally, in this aspect, the apparatus list may display more than one medical apparatus. The apparatus list may include a first medical apparatus and a second medical apparatus that is located near the first medical apparatus. The apparatus list may include a first medical apparatus and a second medical apparatus that are located in the same room. The apparatus list may include a first medical apparatus and a second medical apparatus that are located in the same area of a healthcare facility.

According to a third aspect of the disclosed embodiments, an equipment locating system may include a plurality of medical apparatuses required for patient treatment. A caregiver tag may be coupled to a caregiver in a healthcare facility. A real-time locating system may be configured to determine a location of the caregiver based on a signal received from the caregiver tag. The real-time locating system may determine a location of each of the plurality of medical apparatuses. A display may be configured to notify the caregiver of a task for a patient when the caregiver is determined by the real-time locating system to be within a predetermined proximity to a patient's room. The display may display an apparatus list listing a medical apparatus required for the task along with a corresponding location of the medical apparatus as provided by the real-time locating system. The caregiver may select the medical apparatus from the apparatus list when the medical apparatus is acquired so that the medical apparatus is tagged as being checked out.

In this aspect, the real-time locating system may include a high-accuracy locating system such as an ultra-wideband (UWB) locating system, radio detection and ranging (RADAR) equipment or cameras and/or other imaging equipment or other high-accuracy locating technologies. The medical apparatuses may include, but are not limited to, a mobile lift, a walker, a patient bed, a scanner, for example, a bladder scanner, a glucometer, a respiratory therapy, a VSM, a PCA pump, an spO2 monitor, a language translator, or a fall camera. The display may include a touchscreen display or a display having user inputs, for example, buttons.

In some embodiments of this aspect, the medical apparatus may include an equipment tag that sends a signal to the real-time locating system. The caregiver tag may be at least one of a lanyard or a bracelet. The apparatus list may include a medical apparatus that is closest to the caregiver. The apparatus list may include a medical apparatus that is closest to the patient's room. The apparatus list may include a medical apparatus that is tagged as checked in. The caregiver may tag the medical apparatus as being checked in when the caregiver is finished using the medical apparatus. The caregiver may tag the medical apparatus as requires cleaning when the caregiver is finished using the medical apparatus.

Optionally, in this aspect, the apparatus list may include more than one medical apparatus. The apparatus list may include a first medical apparatus and a second medical apparatus that is located near the first medical apparatus. The apparatus list may include a first medical apparatus and a second medical apparatus that are located in the same room. The apparatus list may include a first medical apparatus and a second medical apparatus that are located in the same area of a healthcare facility.

Accordingly a fourth aspect of the disclosed embodiments, a method of locating equipment in a healthcare facility may include displaying a caregiver menu to select a type of caregiver. The method may also include displaying a patient menu listing patients under the care of the type of caregiver selected from the caregiver menu. The method may also include displaying a task menu listing tasks associated with a patient selected from the patient menu, wherein a medical apparatus is required for the task. The method may also include displaying an apparatus list listing the medical apparatus required for the task along with a corresponding location of the medical apparatus as provided by a real-time locating system. The method may also include selecting the medical apparatus from the apparatus list when the medical apparatus is acquired so that the medical apparatus is tagged as being checked out.

In this aspect, the real-time locating system may include a high-accuracy locating system such as an ultra-wideband (UWB) locating system, radio detection and ranging (RADAR) equipment or cameras and/or other imaging equipment or other high-accuracy locating technologies. The medical apparatuses may include, but are not limited to, a mobile lift, a walker, a patient bed, a scanner, for example, a bladder scanner, a glucometer, a respiratory therapy, a VSM, a PCA pump, an spO2 monitor, a language translator, or a fall camera. The display may include a touchscreen display or a display having user inputs, for example, buttons.

In some embodiments of this aspect, the medical apparatus may include an equipment tag that sends a signal to the real-time locating system. The medical apparatus may include a bar code. The method may also include scanning the bar code to tag the medical apparatus as being checked out. The type of caregiver may include at least one of a doctor, a nurse, a technician, or a housekeeper. The medical apparatus may include more than one medical apparatus. The method may also include displaying each of the more than one medical apparatus in the apparatus list. The method may also include displaying the location of the medical apparatus that is closest to the caregiver. The method may also include determining the location of the caregiver with the real-time locating system.

Optionally, in this aspect, a caregiver tag may be provided. The method may also include determining the location of the caregiver based on a signal received from the caregiver tag. The caregiver tag may be at least one of a lanyard or a bracelet. The method may also include displaying the location of the medical apparatus that is closest to the patient's room. The method may also include displaying a medical apparatus that is tagged as checked in. The method may also include tagging the medical apparatus as checked in when the caregiver is finished using the medical apparatus. The method may also include tagging the medical apparatus as requires cleaning when the caregiver is finished using the medical apparatus.

It may be contemplated, in this aspect, that the apparatus list includes a first medical apparatus and a second medical apparatus that is located near the first medical apparatus. The method may also include displaying a first medical apparatus and a second medical apparatus that are located in the same room. The method may also include displaying a first medical apparatus and a second medical apparatus that are located in the same area of a healthcare facility.

According to a fifth aspect of the disclosed embodiments, an equipment locating system may include a plurality of medical apparatuses required for patient treatment and having equipment tags. A real-time locating system may be configured to determine a location of each of the plurality of medical apparatuses by receiving a signal from the equipment tags. The real-time locating system may include a plurality of receivers mounted at fixed locations and in wireless communication with the equipment tags. The real-time locating system may also include at least one computer communicatively coupled to the plurality of receivers. The equipment tags, the plurality of receivers, and the at least one computer may cooperate to form a high-accuracy locating system operable to determine a location of the equipment tags. A display on a caregiver device may be configured to display a caregiver menu to select a type of caregiver. The display may display a patient menu listing patients under the care of the type of caregiver selected from the caregiver menu. The display may display a task menu listing tasks associated with a patient selected from the patient menu. A medical apparatus of the plurality of medical apparatuses may be required for the task. The display may display an apparatus list listing the medical apparatus required for the task along with a corresponding location of the medical apparatus as provided by the real-time locating system. The caregiver may select the medical apparatus from the apparatus list when the medical apparatus is acquired so that the medical apparatus is tagged as being checked out.

In this aspect, the real-time locating system may include a high-accuracy locating system such as an ultra-wideband (UWB) locating system, radio detection and ranging (RADAR) equipment or cameras and/or other imaging equipment or other high-accuracy locating technologies. The medical apparatuses may include, but are not limited to, a mobile lift, a walker, a patient bed, a scanner, for example, a bladder scanner, a glucometer, a respiratory therapy, a VSM, a PCA pump, an spO2 monitor, a language translator, or a fall camera. The display may include a touchscreen display or a display having user inputs, for example, buttons.

In some embodiments of this aspect, the medical apparatus may include a bar code and the caregiver may scan the bar code to tag the medical apparatus as being checked out. The type of caregiver may include at least one of a doctor, a nurse, a technician, or a housekeeper. The medical apparatus of the plurality of medical apparatuses may include more than one medical apparatus. Each of the more than one medical apparatus may be displayed in the apparatus list. The display may list the location of the medical apparatus that is closest to the caregiver. The location of the caregiver may be determined by the real-time locating system.

Optionally, in this aspect, a caregiver tag may be provided. The real-time locating system may determine the location of the caregiver based on a signal received from the caregiver tag. The caregiver tag may be at least one of a lanyard or a bracelet. The display may list the location of the medical apparatus that is closest to the patient's room. Each medical apparatus of the plurality of medical apparatuses may be tagged as at least one of checked in, checked out, or requires cleaning. The apparatus list may include medical apparatuses that are tagged as checked in. The caregiver may tag the medical apparatus as checked in when the caregiver is finished using the medical apparatus. The caregiver may tag the medical apparatus as requires cleaning when the caregiver is finished using the medical apparatus.

It may be desired, in this aspect, that the apparatus list includes a first medical apparatus and a second medical apparatus that is located near the first medical apparatus. The display may list a first medical apparatus and a second medical apparatus that are located in the same room. The display may list a first medical apparatus and a second medical apparatus that are located in the same area of a healthcare facility.

According to a sixth aspect of the disclosed embodiments, an equipment locating system may include a caregiver tag coupled to a caregiver in a healthcare facility. A real-time locating system may be configured to determine a location of the caregiver based on a signal received from the caregiver tag. The real-time locating system may include a plurality of receivers mounted at fixed locations and in wireless communication with the caregiver tag. The real-time locating system may also include at least one computer communicatively coupled to the plurality of receivers. The caregiver tag, the plurality of receivers, and the at least one computer may cooperate to form a high-accuracy locating system operable to determine a location of the caregiver tag. A display on a caregiver device may be configured to notify the caregiver of a task for a patient when the caregiver is determined by the real-time locating system to be within a predetermined proximity of a patient's room. The display may display an apparatus list listing a medical apparatus required for the task along with a corresponding location of the medical apparatus as provided by the real-time locating system. The caregiver may select the medical apparatus from the apparatus list when the medical apparatus is acquired so that the medical apparatus is tagged as being checked out.

In this aspect, the real-time locating system may include a high-accuracy locating system such as an ultra-wideband (UWB) locating system, radio detection and ranging (RADAR) equipment or cameras and/or other imaging equipment or other high-accuracy locating technologies. The medical apparatuses may include, but are not limited to, a mobile lift, a walker, a patient bed, a scanner, for example, a bladder scanner, a glucometer, a respiratory therapy, a VSM, a PCA pump, an spO2 monitor, a language translator, or a fall camera. The display may include a touchscreen display or a display having user inputs, for example, buttons.

In some embodiments of this aspect, the caregiver tag may be at least one of a lanyard or a bracelet. The apparatus list may include a medical apparatus that is closest to the caregiver. The apparatus list may include a medical apparatus that is closest to the patient's room. The apparatus list may include a medical apparatus that is tagged as being checked in. The caregiver may tag the medical apparatus as being checked in when the caregiver is finished using the medical apparatus. The caregiver may tag the medical apparatus as requires cleaning when the caregiver is finished using the medical apparatus.

Optionally, in this aspect, the apparatus list may display more than one medical apparatus. The apparatus list may include a first medical apparatus and a second medical apparatus that is located near the first medical apparatus. The apparatus list may include a first medical apparatus and a second medical apparatus that are located in the same room. The apparatus list may include a first medical apparatus and a second medical apparatus that are located in the same area of a healthcare facility.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
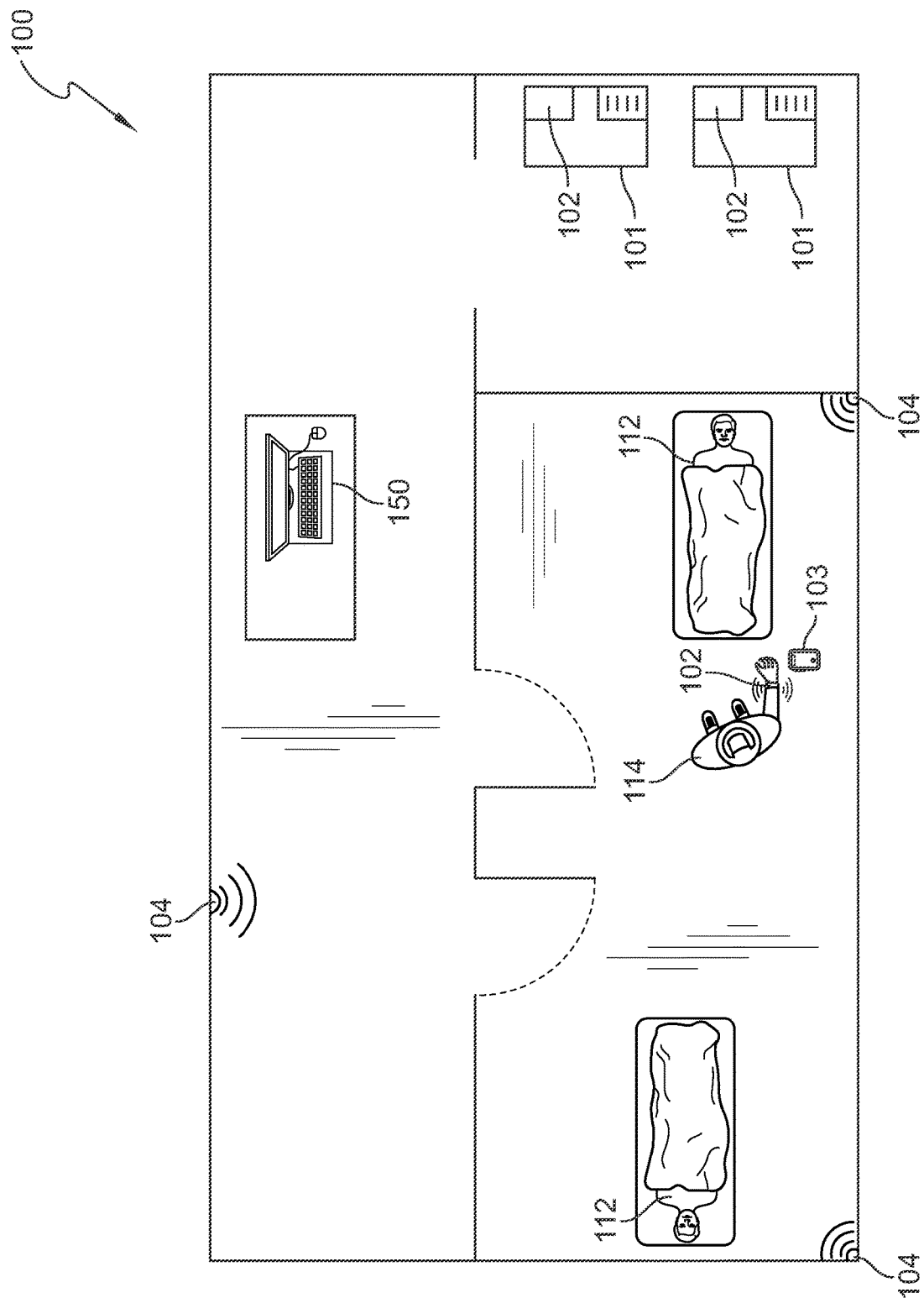
FIG. 1 is a schematic view of a healthcare facility having various patient rooms and storage rooms, wherein a real-time locating system determines a location of caregivers and equipment within the healthcare facility.
Figure 2:
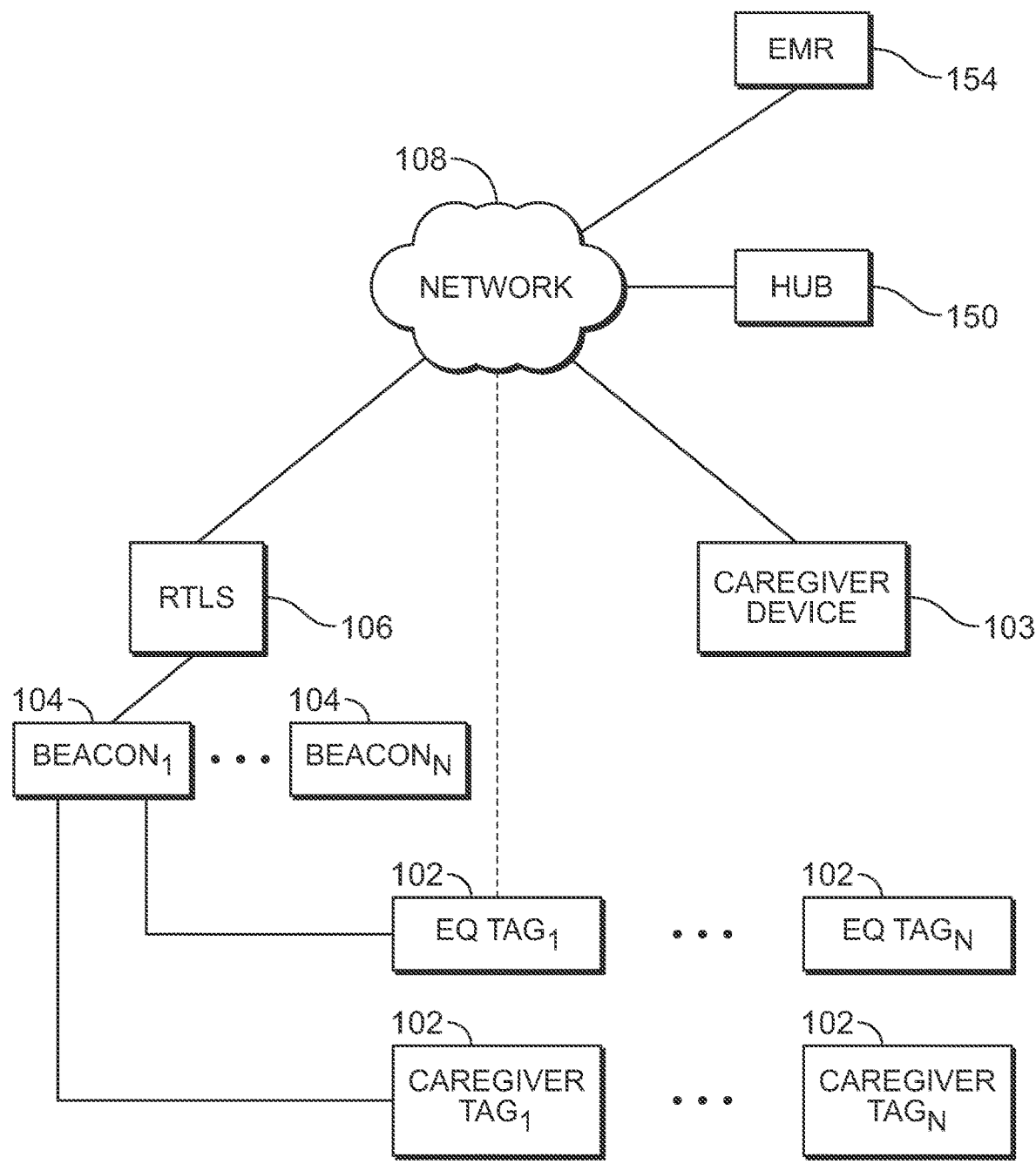
FIG. 2 is a schematic view of an equipment locating system utilized to determine a location of equipment in the healthcare facility and notify a caregiver of equipment locations on a user device.

Referring to FIGS. 1 and 2, an equipment locating system 100 of a healthcare facility is configured to identify equipment 101 required for care of a patient 112 by identifying the necessary equipment 101 on a device 103 of a caregiver 114. The device 103 may be a handheld device, for example, a phone or a tablet, in some embodiments. The system 100 determines a location of the caregiver 114 and enables the caregiver 114 to select a patient 112 near the caregiver 114 on the device 103. In some embodiments, the caregiver 114 is able to select any patient 112 on the device 103. After selecting a patient 112, the device 103 displays a task associated with the patient 112. The caregiver 114 uses the device 103 to select a task and populate a list of equipment 101 required for the task. The system 100 identifies a location of the necessary equipment 101 and displays the location on the device 103.

The illustrated equipment 101 may be any mobile medical apparatus required for the task. For example, the equipment 101 may be a mobile lift, a walker, a patient bed, a scanner, for example, a bladder scanner, a glucometer, a respiratory therapy, a VSM, a PCA pump, an spO2 monitor, a language translator, or a fall camera, in some embodiments. As will be appreciated, any portable medical device known or contemplated in the future may be contemplated by the equipment 101. Although the equipment 101 is illustrated in the room adjacent the patient room, it will be appreciated that the equipment 101 may be located anywhere in the healthcare facility.

The overall system 100 is subdivided into sub-systems which are themselves, also referred to herein as "systems." For example, system 100 includes a locating system, sometimes referred to as a real time locating system (RTLS) in the art, that determines the locations of caregivers 114 and equipment 101 throughout the healthcare facility. In some embodiments, the locating system is embodied as a high-accuracy locating system such as an ultra-wideband (UWB) locating system, but this need not be the case in other embodiments of high-accuracy locating systems such as those using radio detection and ranging (RADAR) equipment or cameras and/or other imaging equipment or other high-accuracy locating technologies.

The illustrative locating system includes a plurality of receivers or transceivers 104 positioned throughout the healthcare facility such as in the patient room, in the hallway of the healthcare facility, and in other locations throughout the healthcare facility (e.g, staff break rooms, bathrooms, pharmacy, treatment rooms, operating rooms, imaging rooms, laboratories, cafeteria, etc.) at the discretion of the system designer. Transceivers 104 each include a receiver and a transmitter. However, in some embodiments, receivers 104 receive wireless transmissions but do not send wireless transmissions. In either case, receivers 104 and transceivers 104, as the case may be, are each configured to receive wireless transmissions. Transceivers 104 and receivers 104 are each communicatively coupled to other components of the locating system such as by use of wired connections like Ethernet cables or other cables.

The transceivers 104 or receivers 104, as the case may be, receive wireless transmissions from caregiver locating tags 102 that are worn by respective caregivers 114 and from equipment tags 102 that are attached to various pieces of equipment such as patient beds 110. Thus, when tag 102 is worn or carried by a caregiver, it is considered to be a caregiver locating tag 102 and when tag 102 is attached to equipment, it is considered to be an equipment locating tag 102. Similarly, when tag 102 is worn or carried by a patient, it is considered to be a patient locating tag 102. In the example of FIG. 1, the caregiver locating tag 102 is coupled to the clothing of the caregiver 114, such as with a clip, and the equipment locating tag 102 is attached to the equipment 101 such as with a fastener (e.g., bolt, screw, snap, hook-and-loop fastener, adhesive, magnet, etc.). Caregiver locating tags 102 may instead be worn around the respective caregivers' necks on a necklace or lanyard or attached to the caregivers' wrists on a wristband or bracelet, for example.

In some embodiments, the tags 102 receive a signal from the transmitter circuitry of one or more of the transceivers 104 and, in response, transmit a return signal to at least one of the transceivers 104. The return signal includes a tag identification (ID) which is unique to each tag 102. Such an arrangement preserves battery life of tags 102 because transmissions of tag ID's are only made by the tags 102 when in communicative proximity of one or more transceivers 104 and after receiving a request signal from at least one of the transceivers 104. In other embodiments, tags 102 operate to transmit their respective tag ID's on a periodic basis for receipt by receivers 104 or transceivers 104, as the case may be. In still other embodiments, short range wireless beacons or infrared transmitters are mounted at fixed locations throughout the healthcare facility and send a signal with a location ID to the tags 102 that are in the vicinity of the short range beacons and, in response to receipt of the signal, the tags 102 transmit their respective tag ID's and the location ID's to transceivers 104 or receivers 104. In each of these embodiments, transceivers 104 or receivers 104 transmit the received tag ID or tag ID's if multiple tags are present, to an RTLS server 106 of the locating system along with a respective transceiver ID and, if applicable, the location ID.

In some embodiments, the transceiver ID's or receiver ID's correlate to particular locations in the healthcare facility. Thus, the RTLS server 106 determines the locations of tags 102 within the healthcare facility by correlating the tag ID's with the transceiver or receiver ID's (and/or the location ID's, if applicable) and, ultimately, with the location correlated with the transceiver or receiver ID's and/or location ID's. RTLS server 106 also correlates the tag ID's with the respective caregivers wearing tags 102 and with the equipment to which tags 102 are attached, as the case may be. In some embodiments, patients 112 also have tags 102 for determining the whereabouts of the patients 112 throughout the healthcare facility as alluded to above. Thus, in some embodiments, the locating system of overall system 100 includes tags 102, transceivers 104 (or receivers 104), and RTLS server 106. Tags 102 are sometimes referred to as "badges" and so the terms "tag" and "badge" are used interchangeably herein.

System 100 includes network infrastructure which is designated diagrammatically as network 108 in FIG. 2. Network 108 is intended to represent the infrastructure (e.g., wireless access points, Ethernet jacks such as RJ-45 connectors, wires, routers, gateways, etc.) provided in a healthcare facility and the various computer devices (e.g., personal computers, servers, laptop computers, patient care equipment, etc.) that are coupled to the infrastructure. The various subsystems described herein include components that may communicate with each other using portions of network 108. In the illustrative example, transceivers 104 or receivers 104 communicate with RTLS server 106 via portions of network 108. In the description that follows, the term transceiver 104 will be used but the description is equally applicable to embodiments having receivers 104 unless specifically noted otherwise.

In some embodiments, tags 102 communicate wirelessly with transceivers 104 using infrared (IR) technology. In such embodiments, line of sight between tags 102 and one or more of transceivers 104 needs to remain unobstructed in order for communication to be established between the tags 102 and one or more of the transceivers 104 to determine the location of the tags 102 in the healthcare facility. Thus, the IR signals cannot pass through walls, equipment, and people located in the room. In general, locating systems that use IR communication between tags 102 and transceivers 104 are able to reliably determine that the tags 102 are located inside a particular room, but are not able to determine the exact location, within a relatively small accuracy threshold, of the tag 102 within the room.

As noted above, the locating system in some embodiments is embodied as a high-accuracy locating system such as an ultra-wideband (UWB) locating system. In such embodiments, tags 102 are configured as UWB tags 102 having UWB transceivers or transmitters, and transceivers 104 are configured as UWB transceivers or UWB receivers. The description that follows refers to UWB transceivers 104 but is equally applicable to embodiments using UWB receivers 104 unless specifically noted otherwise.

The UWB transceivers 104 are stationary and the UWB transceivers of tags 102 are mobile, but their circuitry otherwise may be substantially the same. Thus, tags 102 and transceivers 104 each include a housing that contains associated circuitry. The circuitry of tags 102 and transceivers 104 includes, for example, a processor such as a microprocessor or microcontroller or the like, memory for storing software, and communications circuitry including a transmitter, a receiver and at least one antenna. Transceivers 104 each include mounting hardware, such as brackets or plates or the like, in some embodiments, to permit the transceivers 104 to be mounted at fixed locations in the patient rooms and other locations of the healthcare facility with fasteners such as screws or the like.

In the illustrative example of system 100 of FIG. 1, the high-accuracy locating system further includes a UWB hub computer 150 which is communicatively coupled to other UWB hub computers 150 of the high-accuracy locating system via network 108 of the healthcare facility. UWB hub computer 150 serves as an intermediary between transceivers 104 and RTLS server 106. Of course, the other UWB hub computers 150 are also communicatively coupled to respective sets of transceivers 104. In the illustrative example, the high-accuracy locating system is also communicatively coupled to the device 103 and to other servers or computers of the healthcare facility, such as to an EMR server 154 or an admission/discharge/transfer (ADT) computer, just to name a couple.

Figure 3:
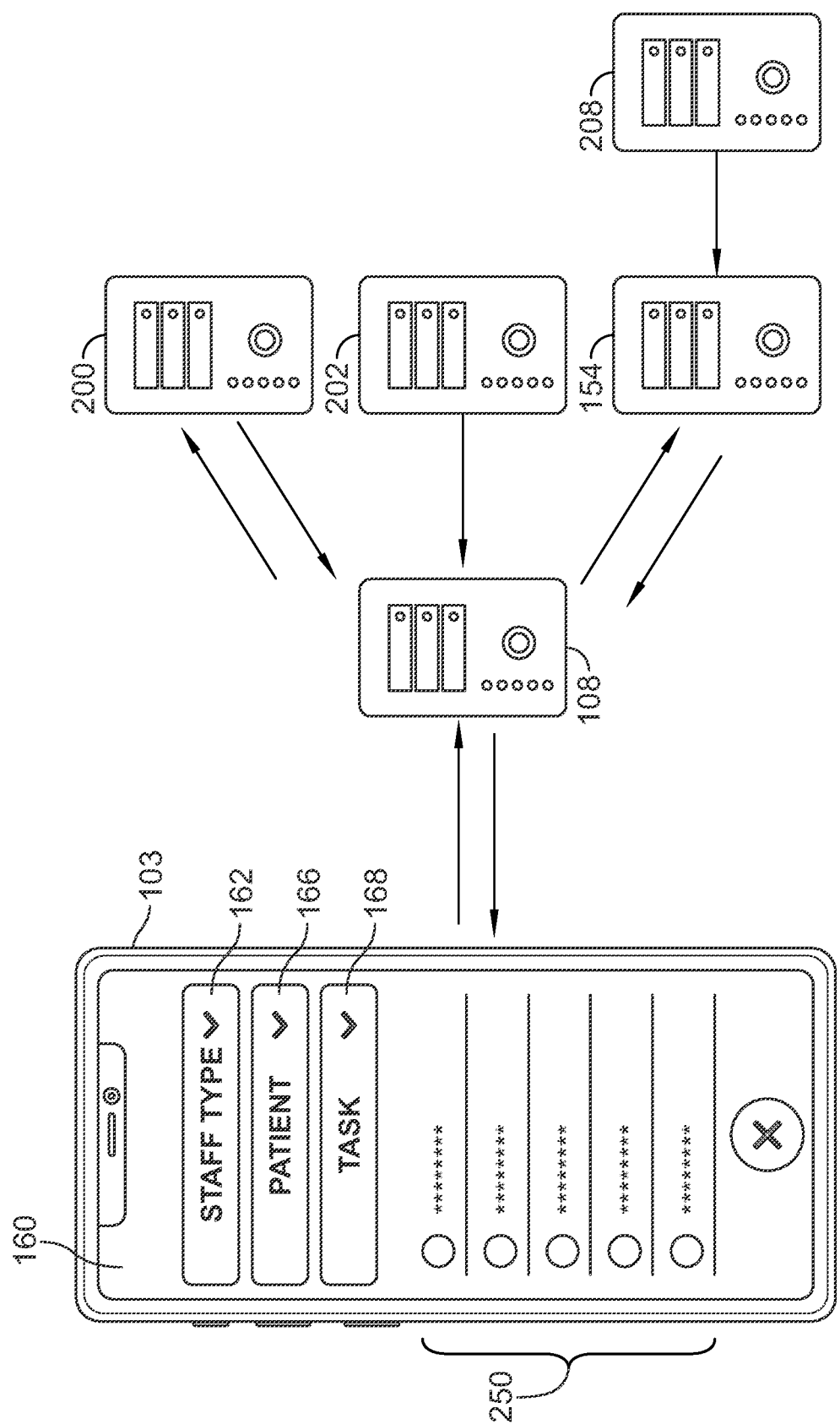
FIG. 3 is another schematic view of the equipment locating system showing various servers in communication with the user device.
Figure 4:
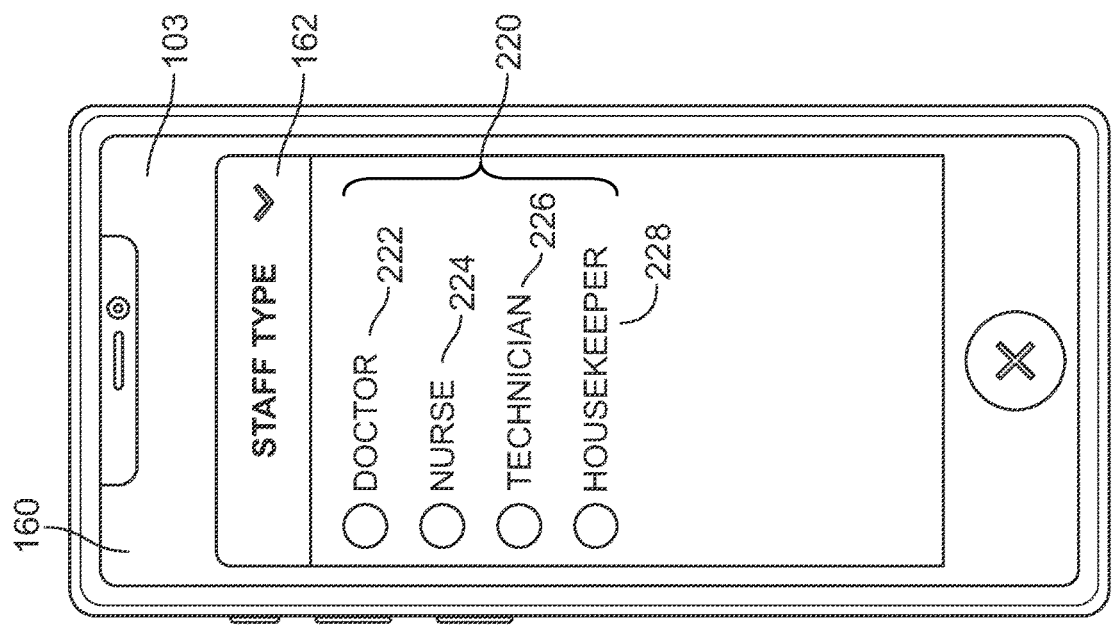
FIG. 4 is a view of a display on the user device showing a caregiver list to select a type of caregiver.

Referring to FIG. 3, the device 103 includes a display 160 that may be embodied as a touch screen display, as illustrated. In some embodiments, the device 103 may include buttons or dials for the caregiver to navigate through various menus. In the illustrative embodiment, the display 160 includes a caregiver menu 162 that lists all of the caregivers 114 on duty. In some embodiments, the caregiver menu 162 may only list those caregivers within a particular department, for example, the emergency room. In another embodiment, the caregiver menu 162 is not provided and only patients and tasks assigned to the caregiver 114 to whom the device belongs are displayed. FIG. 4 illustrates an exemplary caregiver list 220 that may be populated by selecting the caregiver menu 162. In the illustrative embodiment, the caregiver list 220 includes selections for doctor 222, nurse 224, technician 226, and housekeeper 228. The user of device 103 selects the entry that corresponds to their position by pressing the entry or swiping the entry. It should be noted that other types of caregivers 114 may be contemplated. In some embodiments, the caregiver list 220 lists the names of the caregivers 114. For example, if multiple doctors and nurses are assigned to a department, the caregiver list 220 may display each doctor and nurse by name.

Figure 5:
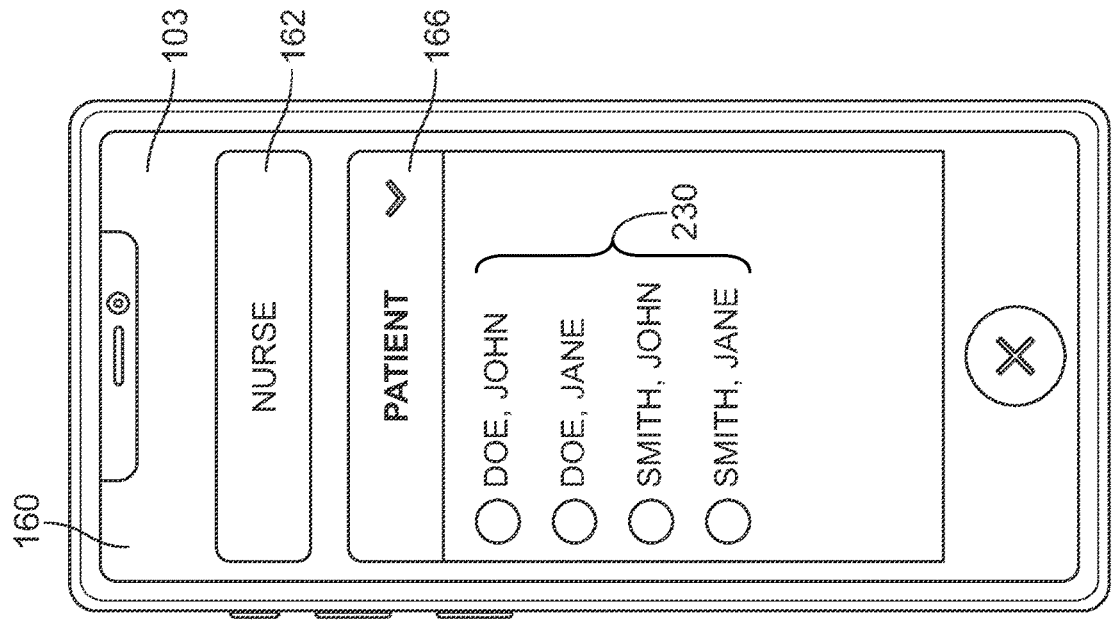
FIG. 5 is a view of a display on the user device showing a patient list to select a patient under the care of a caregiver.

A patient menu 166 (shown in FIG. 3) shows a list of patients 112 currently admitted to the healthcare facility. In some embodiments, the patient menu 166 only lists those patients 112 admitted in a particular department of the healthcare facility, i.e. the emergency room. In yet another embodiment, the patient menu 166 only provides the names of patients 112 under the care of a caregiver 114 selected from the caregiver menu 162. In an embodiment that does not include a caregiver menu, the patient menu 166 may only list the patients 112 of the caregiver 114 to whom the device 103 belongs. FIG. 5 illustrates and exemplary patient list 230 that is populated by selecting the patient menu 166. The patient list 230 includes the name of each patient 112 assigned to the respective caregiver 114. To select a patient 112, the caregiver 114 may press or swipe the patient name.

In some embodiments, the patient list 230 is limited by a location of the caregiver 114. In such an embodiment, the system 100 determines the location of the caregiver 114 and only lists the patients 112 within a predetermined distance to the caregiver 114. For example, the patient list 230 may only list the patients 112 within a predetermined radius to the caregiver 114. In another example, the patient list 230 may only list the patients 112 within the same department or area of the healthcare facility in which the caregiver 114 is positioned. The caregiver 114 may be able to alter the settings of the device 103 to display all patients 112 under their care or only patients 112 within a predetermined area.

Figure 6:
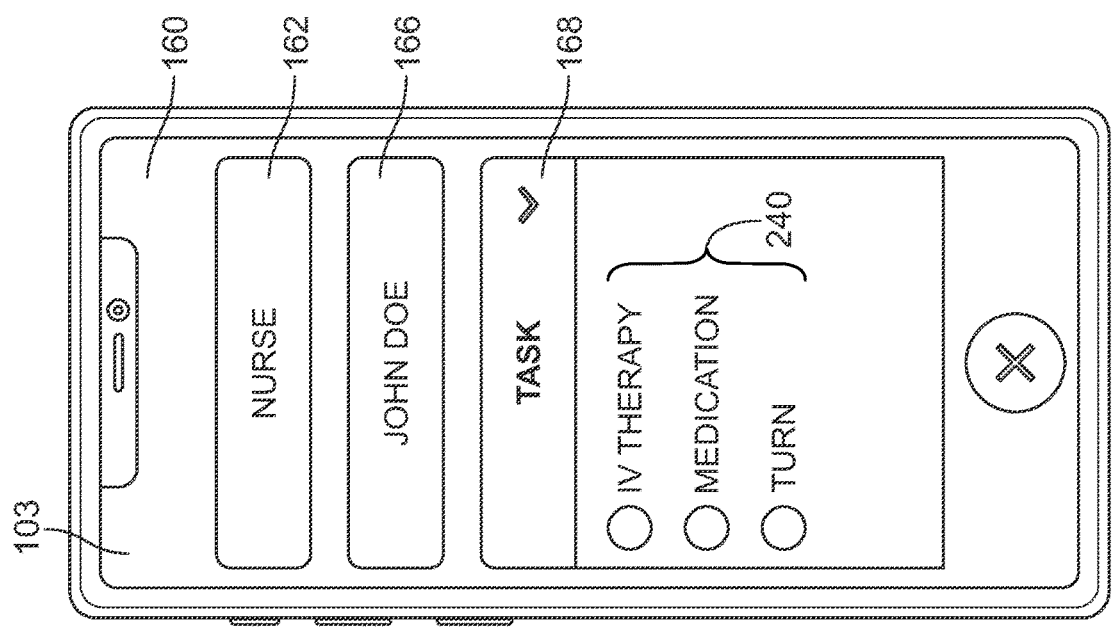
FIG. 6 is a view of a display on the user device showing a task list to select a task for a patient selected in the patient list.

A task menu 168 (shown in FIG. 3) provides a list of tasks for each patient 112. For example, the task menu 168 may list all tasks to be accomplished in the healthcare facility or in a particular department. In some embodiments, the task menu 168 lists only the tasks required for the patient 112 selected in the patient menu 166. Upon selecting a task from the task menu 168, an equipment list 250 is populated to display each piece of equipment 101 required for the task. FIG. 6 illustrates an exemplary task menu 240 that is displayed after selecting a patient from the patient list 230. The task menu 240 includes all uncompleted tasks related to the patient 112. In the exemplary embodiment, a nurse has been selected as the caregiver for John Doe. The task list 240 includes IV therapy, medication, and turning the patient. Each of these tasks may be selected by pressing or swiping the task.

Figure 7:
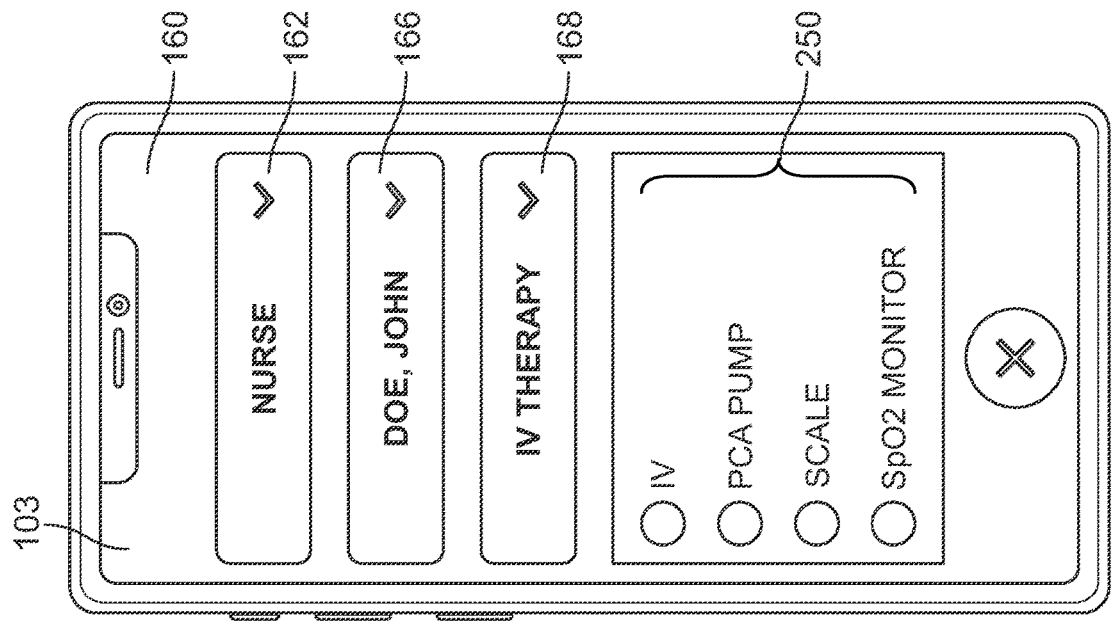
FIG. 7 is a view of a display on the user device showing an equipment list to select equipment required for the task selected in the task list.
Figure 8:
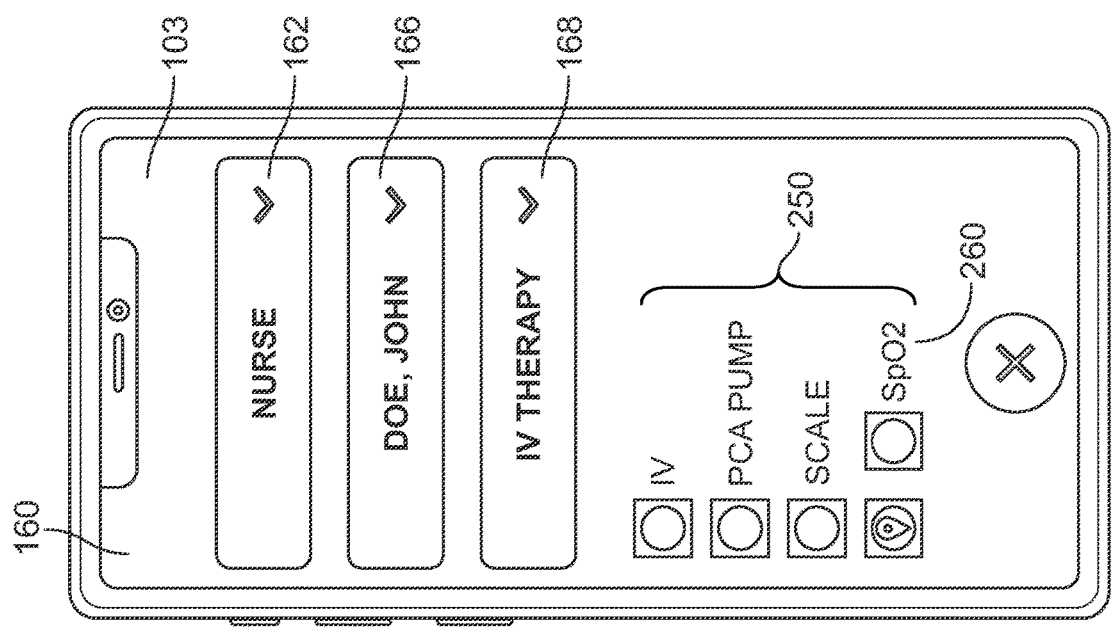
FIG. 8 is a view of a display on the user device showing the selected equipment from the equipment list.

FIG. 7 illustrates an exemplary equipment list 250. In the illustrative embodiment, the equipment list 250 for IV therapy includes an IV, a PCA pump, a scale, and an SpO2 monitor. The caregiver 114 can select a piece of equipment 101 by pressing or swiping the equipment 101 in the equipment list 150, as shown in FIG. 8, wherein the SpO2 monitor 260 has been selected. The caregiver 114 is then notified of a location of the equipment.

In some embodiments, the patient list 230 is only available after selecting a caregiver from the caregiver list 220. Likewise, the task list 240 may only be available after selecting a patient 112 from the patient list 230. In a similar manner, an equipment list 250 may only populate after selecting a task from the task list 240.

Referring back to FIG. 3, the device 103, is connected to various systems through the network 108. A rounding server 200 provides information related to caregivers 114 on duty and tasks for their patients. For example, the rounding server 200 may cause all caregiver tasks to be displayed or may only cause the tasks associated with a selected caregiver to display. Once a task is completed, the caregiver 114 can notify the rounding server 200 to remove the task.

An ADT feed 202 transmits data related to the patient 112 to the device 103. For example, the data may include bibliographic data, health history, etc. While this data is delivered to the device 103, in the illustrative embodiment, the caregiver 114 cannot utilize the device 103 to alter the data. In some embodiments, the caregiver 114 may have the option to edit the patient data and send the edits back to the ADT feed 202.

The EMR server 154 sends data to and receives data from the device 103. The EMR server 154 may document the equipment 101 in use, as well as, billing for the equipment 101. The EMR server 154 also documents tasks that have been completed. The EMR server 154 is in communication with an order entry server 208 that determines medication, therapy, and treatment orders. For example, a doctor may enter an order for a blood draw into the order entry server 208. This order is communicated to the device 103 through the EMR server 154 so that the ordered blood draw is including in the task menu 168.

Figure 9:
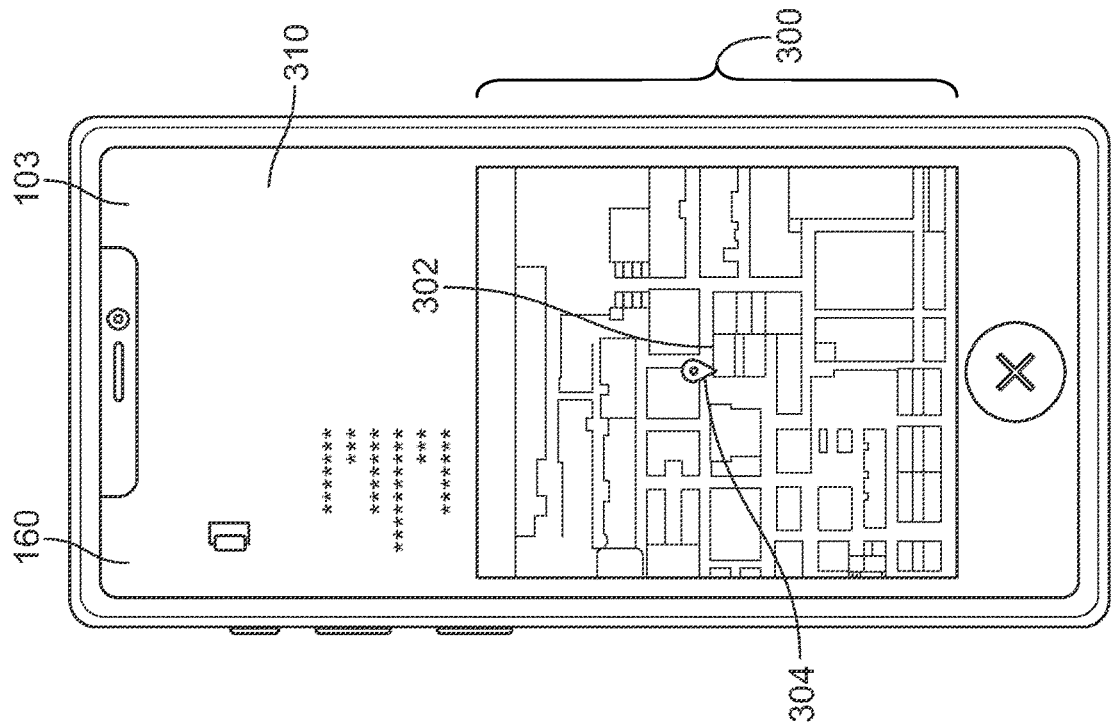
FIG. 9 is a view of a display on the user device showing a map with an icon representing the location of the equipment selected from the equipment list and an icon representing the location of the caregiver selected from the caregiver list.

Referring to FIG. 9, upon selecting a piece of equipment 101 from the equipment list 250, a map 300 of the healthcare facility is displayed on the display 160. The map 300 includes an icon 302 showing the location of the equipment 101 and an icon 304 showing the position of the caregiver 114. Data 310 related to the equipment 101 is also displayed above the map 300. In an exemplary embodiment, the equipment 101 may be tagged as "not in use," "in use," or "requires cleaning." The map 300 only includes the location of equipment 101 that is "not in use." In this manner, the caregiver 114 avoids locating equipment 101 that is not available. Further, the map 300 may only display the equipment 101 that is closest to the caregiver 114 so that the caregiver 114 can save time in obtaining the equipment 101. In some embodiments, the task may require multiple pieces of equipment 101. In such a scenario, the system 100 identifies the necessary pieces of equipment 101 that are located near each other. For example, the map 300 may only display a first piece of equipment 101 and a second piece of equipment 101 that are in the same area of the healthcare facility or in the same room. The system 100 identifies the pieces of equipment 101 that are closest to reduce time spent gathering the equipment 101.

Figure 10:
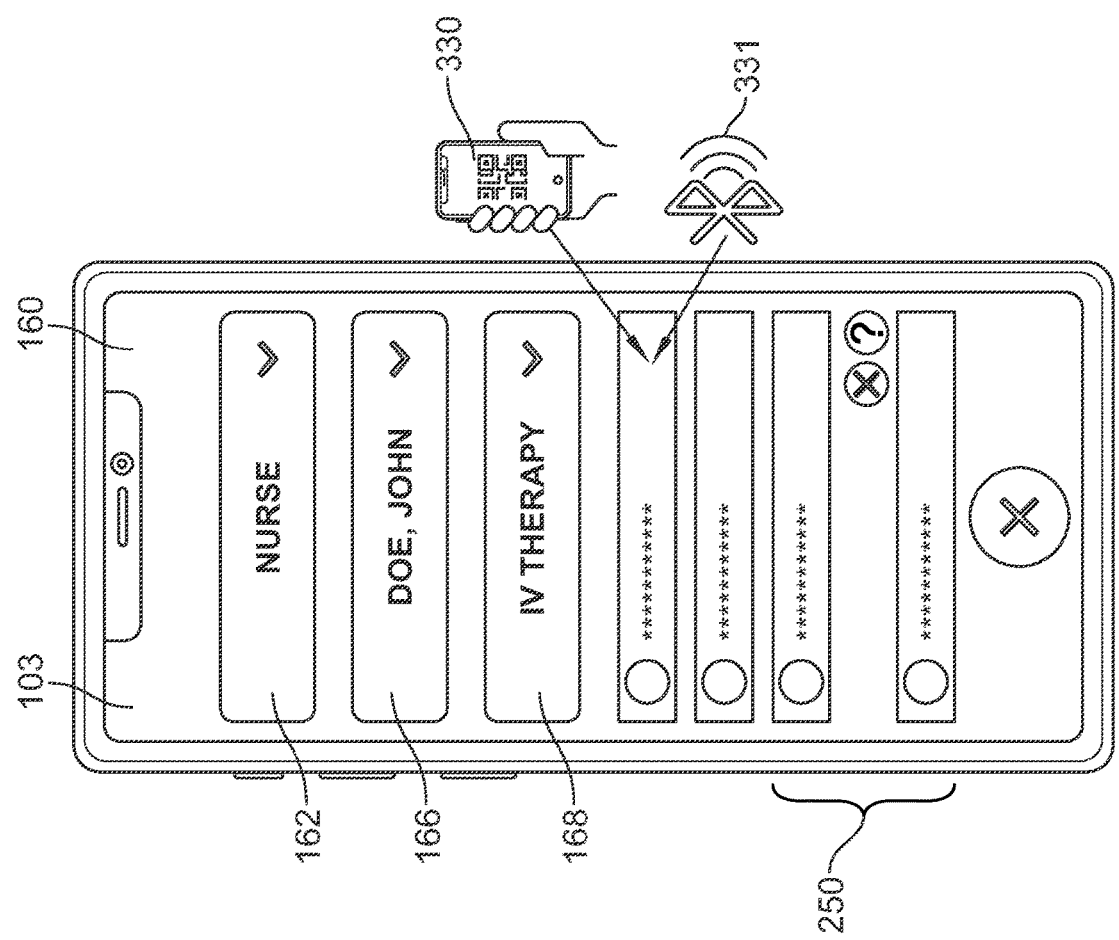
FIG. 10 is a view of a display on the user device showing information icons that are selectable to display information related to the equipment selected in the equipment list.
Figure 11:
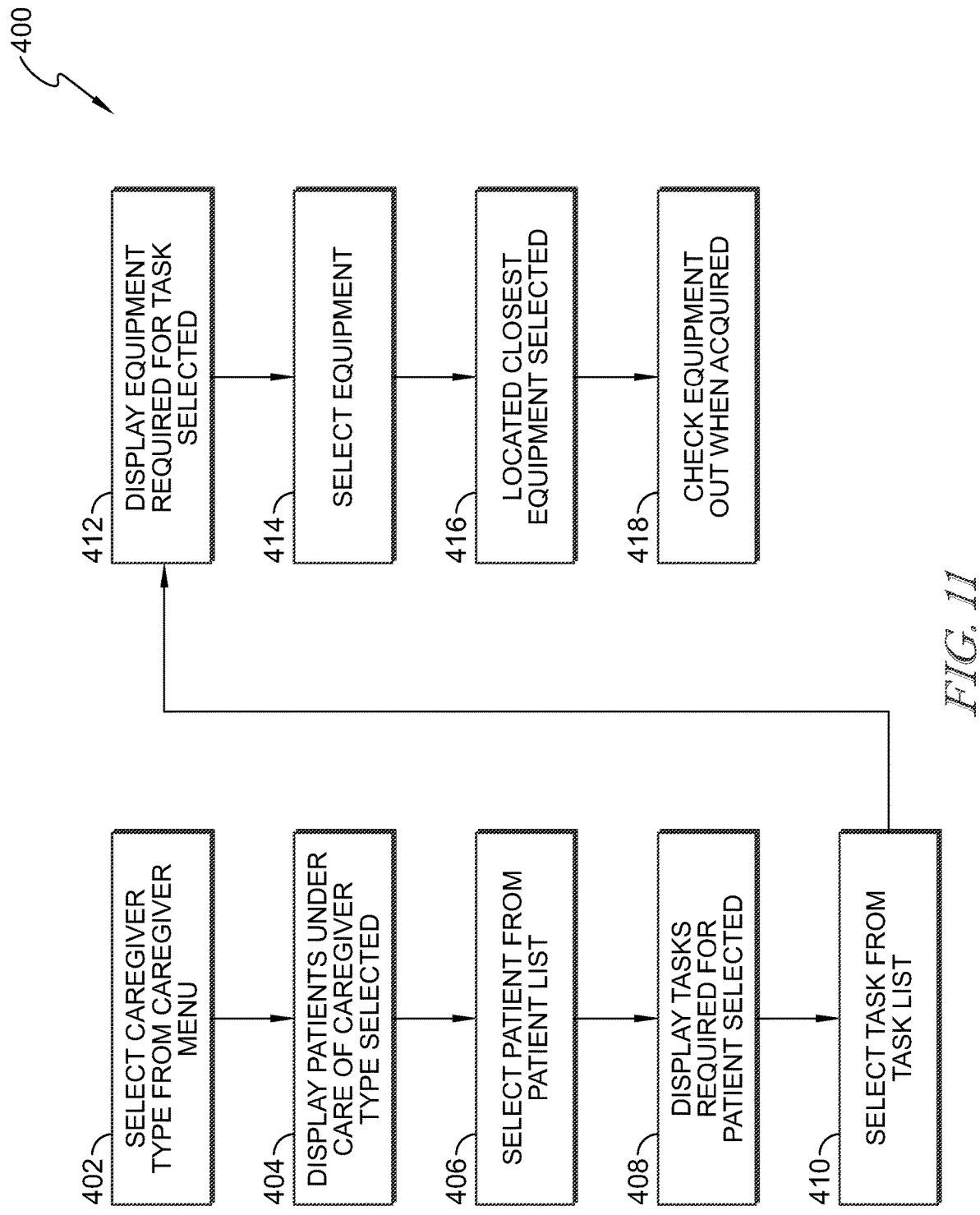
FIG. 11 is a flowchart of a method for utilizing the equipment locating system.

When the caregiver 114 acquires the necessary equipment 101, the caregiver may tag the equipment as "in use" so that other caregivers do not try to acquire the same piece of equipment 101. This tagging is accomplished either through the device 103 and/or by scanning a bar code 320 (shown in FIG. 1) on the equipment 101. As illustrated in FIG. 10, a QR code 330 is populated in the device 103 to enable the caregiver 114 to scan the equipment 101. The QR code 330 can also be scanned to populated information, such as instructions, related to the equipment 101. In the illustrative embodiment, the device 103 may also be Bluetooth enabled 331. The display 160 also includes an information icon 332 that populates information, such as instructions and troubleshooting. Upon returning the equipment 101, the caregiver 114 can check the equipment 101 in as "not in use" or "requires cleaning." If the equipment is tagged as "requires cleaning," a technician or housekeeper may be notified.

Referring now to FIG. 10, a flowchart 400 illustrates a method for utilizing the system 100. At block 402, the user of the device 103 selects a caregiver 114 from the caregiver list 220. The user may select a type of caregiver 220, i.e. doctor, nurse, technician, or housekeeper. Alternatively, the user may select a caregiver 114 by name. In some embodiments, block 402 may be skipped as only the caregiver 114 to whom the device 103 belongs may be automatically selected.

Upon selecting a caregiver 114, the display 160 shows the patient list 230 listing the patients 112 under the care of the selected caregiver 114, at block 404. In some embodiments, all of the patients 112 under the care of the caregiver 114 are displayed in the patient list 230. In other embodiments, only patients 112 within the predetermined area near the caregiver 114 are listed. At block 406, the user selects a patient 112 from the patient list 230 and the task list 240 is populated, at block 408. The task list 240 includes all of the tasks required for the selected patient 112.

At block 410, the user selects a task from the task list 240, and, at block 412, the equipment 101 required for the task is populated in the equipment list 250. The user then selects at least one piece of equipment, at block 414. At block 416, the system 100 identifies the closest equipment 101 needed and displays the map 300. When more than one piece of equipment 101 is selected, the system 100 identifies the pieces of equipment 101 that are closest to one another, for example, in equipment 101 in the same room or equipment 101 in the same area of the healthcare facility. The system 100 may only display the equipment 101 that is "not in use" or "available for use." When the user acquires the needed equipment 101, the equipment 101 is checked out, at block 418, as set forth above. The system 100 then tags the equipment 101 as "in use."

Figure 12:
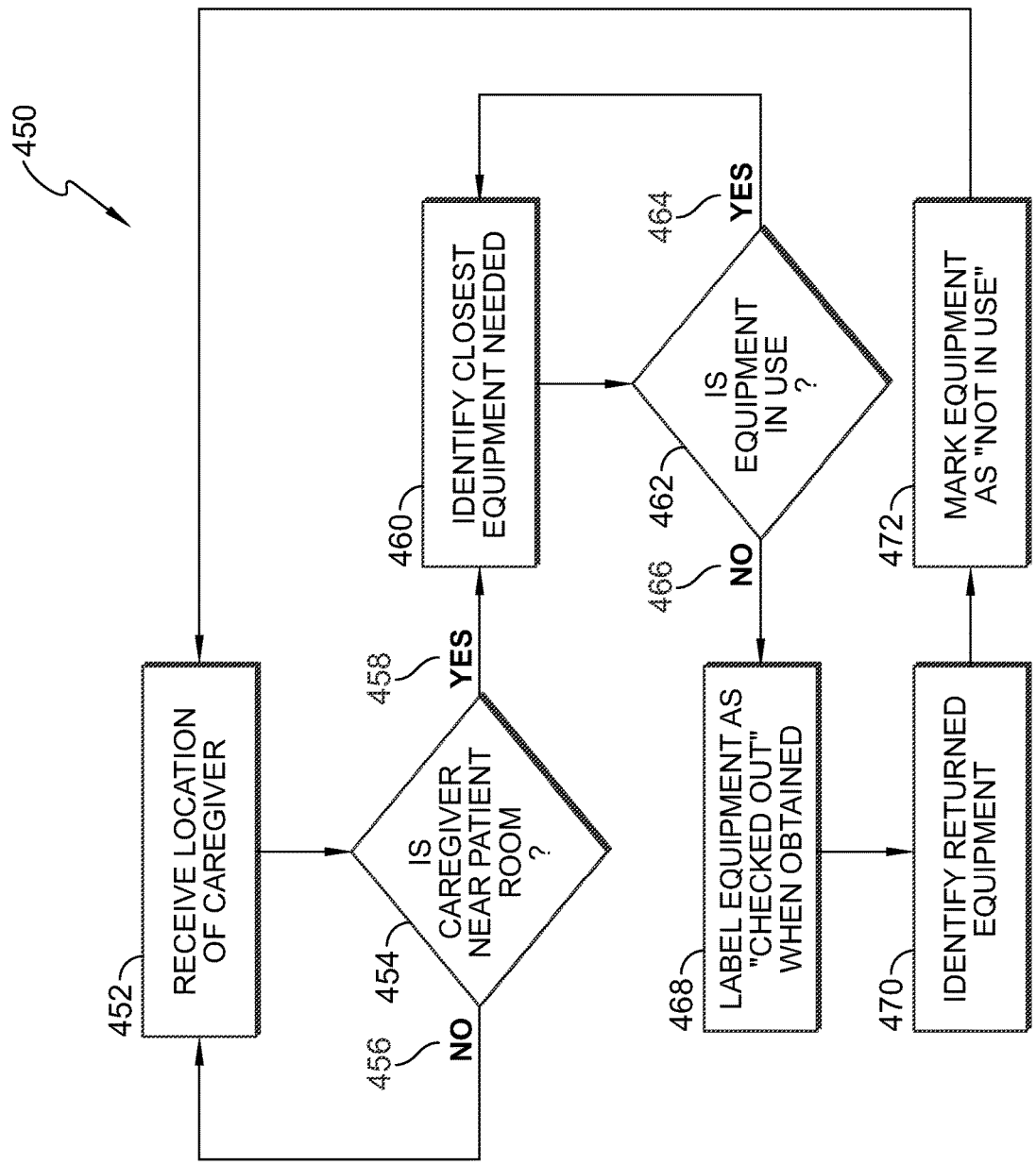
FIG. 12 is another flowchart of a method for utilizing the equipment locating system.

FIG. 12 illustrates a flowchart 450 of one operation of the system 100. At block 452, the system 100 determines a location of the caregiver 114. The system 100 determines whether the caregiver 114 is near a patient room housing a patient 112 in need of care, at block 454. The system 100 may determine if the caregiver 114 is in a patient room, within a predetermined distance to a patient room, or within the same area or department of the healthcare facility as the patient room. If the caregiver 114 is not, at 456, in the same area as a patient 112, the system 100 continues to continue determining the location of the caregiver 114.

If the caregiver 114 is in the same area as the patient 112, at 458, the system 100 identifies the necessary equipment 101 needed for patient care, at block 460. At block 462, the system 100 determines whether the equipment 101 is "in use" or otherwise unavailable. If the equipment 101 is "in use" or otherwise unavailable, at block 464, the system 100 identifies the next closest piece of equipment 101. If the equipment 101 is not "in use," at block 466, the system 100 notifies the caregiver 114 of the location of the equipment 101. Upon acquiring the necessary equipment 101, the caregiver 114 checks the equipment out, as set forth above. The system 100 then tags the equipment 101 as "checked out" or "in use," at block 468

When the caregiver 114 is done using the equipment 101, the caregiver 114 notifies the system 100 by scanning the equipment or utilizing the device to check the equipment in. At block 470, the system 100 identifies the checked in equipment 101. If the equipment 101 requires cleaning the system 100 may tag the equipment 101 as such. Otherwise, the system 100 tags the equipment 101 as "not in use," at block 472. The equipment 101 then becomes available for future use.

Although this disclosure refers to specific embodiments, it will be understood by those skilled in the art that various changes in form and detail may be made without departing from the subject matter set forth in the accompanying claims.

The invention claimed is:

1. An equipment locating system comprising:
a plurality of medical apparatuses required for patient treatment and having equipment tags,
a real-time locating system configured to determine a location of each of the plurality of medical apparatuses by receiving a signal from the equipment tags, and
a display configured to display a caregiver menu to select a type of caregiver,
wherein the display is configured to display a patient menu listing patients under the care of the type of caregiver selected from the caregiver menu,
wherein the display is configured to display a task menu listing tasks associated with a patient selected from the patient menu, wherein a medical apparatus of the plurality of medical apparatuses is required for the task,
wherein the display is configured to display an apparatus list listing the medical apparatus required for the task along with a corresponding location of the medical apparatus as provided by the real-time locating system,
wherein the display is configured to display a map including an icon showing a location of the medical apparatus and a position of the caregiver,
wherein the medical apparatus is configured to be selected from the apparatus list by the caregiver when the medical apparatus is acquired so that the medical apparatus is tagged as being checked out, and
wherein the display is configured to display and update the map to show the medical apparatus as being in use after being checked out.

2. The system of claim 1, wherein the medical apparatus includes a bar code configured to be scanned by the caregiver to tag the medical apparatus as being checked out.

3. The system of claim 1, wherein the type of caregiver includes at least one of a doctor, a nurse, a technician, or a housekeeper.

4. The system of claim 1, wherein the medical apparatus of the plurality of medical apparatuses includes more than one medical apparatus, wherein each of the more than one medical apparatus is displayed in the apparatus list.

5. The system of claim 1, wherein the display is configured to list the location of the medical apparatus that is closest to the caregiver.

6. The system of claim 1, wherein the location of the caregiver is determined by the real-time locating system.

7. The system of claim 6, further comprising a caregiver tag, wherein the real-time locating system is configured to determine the location of the caregiver based on a signal received from the caregiver tag.

8. The system of claim 1, wherein the display is configured to list the location of the medical apparatus that is closest to the patient's room.

9. The system of claim 1, wherein each medical apparatus of the plurality of medical apparatuses is tagged as at least one of checked in, checked out, or requires cleaning.

10. The system of claim 1, wherein the apparatus list includes medical apparatuses that are tagged as checked in.

11. The system of claim 1, wherein the medical apparatus is configured to be tagged by the caregiver as at least one of checked in and requires cleaning when the caregiver is finished using the medical apparatus.

12. The system of claim 1, wherein the apparatus list includes a first medical apparatus and a second medical apparatus that is located near the first medical apparatus.

13. The system of claim 1, wherein the display lists is configured to list a first medical apparatus and a second medical apparatus that are located in at least one of the same room and in the same area of a healthcare facility.

14. An equipment locating system comprising:
a caregiver tag coupled to a caregiver in a healthcare facility,
a real-time locating system configured to determine a location of the caregiver based on a signal received from the caregiver tag, and
a display configured to notify the caregiver of a task for a patient when the caregiver is determined by the real-time locating system to be within a predetermined proximity of a patient's room,
wherein the display is configured to display an apparatus list listing a medical apparatus required for the task along with a corresponding location of the medical apparatus as provided by the real-time locating system,
wherein the display is configured to display a map including an icon showing a location of the medical apparatus and a position of the caregiver,
wherein the medical apparatus is configured to be selected from the apparatus list by the caregiver when the medical apparatus is acquired so that the medical apparatus is tagged as being checked out, and
wherein the display is configured to display and update the map to show the medical apparatus as being in use after being checked out.

15. The system of claim 14, wherein the apparatus list includes a medical apparatus that is at least one of closest to the caregiver and closest to the patient's room.

16. The system of claim 14, wherein the apparatus list includes a medical apparatus that is tagged as being checked in.

17. The system of claim 14, wherein the medical apparatus is configured to be tagged by the caregiver as being at least one of checked in and requires cleaning when the caregiver is finished using the medical apparatus.

18. The system of claim 14, wherein the apparatus list is configured to display more than one medical apparatus.

19. The system of claim 14, wherein the apparatus list includes a first medical apparatus and a second medical apparatus that is located near the first medical apparatus.

20. The system of claim 14, wherein the apparatus list includes a first medical apparatus and a second medical apparatus that are located in at least one of the same room and in the same area of a healthcare facility.

* * * * *

UNITED STATES PATENT AND TRADEMARK OFFICE
CERTIFICATE OF CORRECTION

PATENT NO. : 11,610,671 B2
APPLICATION NO. : 17/015209
DATED : March 21, 2023
INVENTOR(S) : Ryan Hochworter It is certified that error appears in the above-identified patent and that said Letters Patent is hereby corrected as shown below:

In the Claims

In Column 14, Line 40, Claim 13, after the word "display" delete the word "lists".

Signed and Sealed this
Sixteenth Day of May, 2023

Katherine Kelly Vidal
*Director of the United States Patent and Trademark Office*